United States Patent

Svara

Patent Number: 5,214,178
Date of Patent: May 25, 1993

[54] CYCLIC ACYLPHOSPHINIC ACID DERIVATIVES AND PROCESS FOR THEIR PREPARATION

[75] Inventor: Jürgen Svara, Cologne, Fed. Rep. of Germany

[73] Assignee: Hoechst Aktiengesellschaft, Frankfurt am Main, Fed. Rep. of Germany

[21] Appl. No.: 878,178

[22] Filed: May 4, 1992

[30] Foreign Application Priority Data

May 16, 1991 [DE] Fed. Rep. of Germany ....... 4115947

[51] Int. Cl.$^5$ .............................. C07F 9/6574
[52] U.S. Cl. ........................ 558/82; 558/95; 558/96
[58] Field of Search ................. 558/82, 96, 95, 82

Primary Examiner—Joseph Paul Brust
Assistant Examiner—Michael G. Ambrose
Attorney, Agent, or Firm—Connolly & Hutz

[57] ABSTRACT

The invention relates to novel cyclic acylphosphinic acid derivatives of the formula

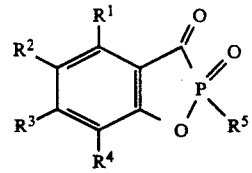

in which the substituents independently of each other can have the following meaning:

$R^1$, $R^2$, $R^3$, $R^4$ = H, Cl, Br or C1- to C10-alkyl or -alkoxy but on condition that either $R^1$ and $R^2$ together, or $R^3$ and $R^4$ together, with incorporation of the associated aromatic 6-ring, form a naphthalene structure;

$R^5$ = C1- to C4-alkyl, C5- or C6-cycloalkyl, phenyl or alkylphenyl.

The novel cyclic acylphosphinic acid derivatives can be prepared by reacting the corresponding aromatic o-hydroxycarboxylic acids with organyldichlorophosphines of the formula $R^5PCl_2$ in an aprotic solvent or suspension medium at 0° to 200° C. with elimination of HCl and by separating off and purifying the precipitated target product.

4 Claims, No Drawings

CYCLIC ACYLPHOSPHINIC ACID DERIVATIVES AND PROCESS FOR THEIR PREPARATION

The invention relates to novel cyclic acylphosphinic acid derivatives of the formula

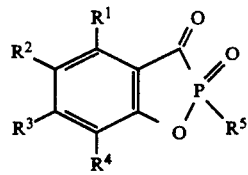

in which the substituents independently of each other can have the following meaning:

$R^1$, $R^2$, $R^3$, $R^4$ = H, Br or C1- to C10-alkyl or -alkoxy, but on condition that either $R^1$ and $R^2$ together, or $R^3$ and $R^4$ together, with incorporation of the associated aromatic 6-ring, form a naphthalene structure;

$R^5$ = C1- to C4-alkyl, C5- or C6-cycloalkyl, phenyl or alkylphenyl.

The substituents $R^1$ and $R^2$ or $^3$ and $R^4$ must in each case together form a benzo group, that is the aromatic benzene unit present is extended to form an aromatic naphthalene unit. Possible substituents in this extended aromatic ring system can be for example one or more C1- to C10-alkyl or -alkoxy groups.

The novel cyclic acylphosphinic acid derivatives are usable as photoinitiators.

The invention also further relates to a process for the preparation of the novel cyclic acylphosphinic acid derivatives mentioned, which comprises reacting aromatic o-hydroxycarboxylic acids of the formula

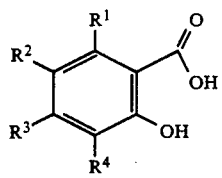

or their alkali metal salts with organyldichlorophosphines of the formula $R^5PCl_2$, where $R^1$, $R^2$, $R^3$, $R^4$ and $R^5$ have the meaning given, in an aprotic solvent or suspension medium at temperatures of 0° to 200° C., preferably 20° to 150° C., with liberation of gaseous hydrogen chloride or precipitation of alkali metal chloride and separating off the precipitated target product and purifying it in a method known per se.

Aprotic solvents or suspension media are those which are inert to a P—Cl group and HCl, for example toluene, xylene, halogenated hydrocarbons, petroleum ether, alkanes, ethers (methyl tert-butyl ether, diisopropyl ether, glycol ether) or ether esters of glycol (for example methyl glycol acetate). The aprotic solvents or suspension media to be used must, of course, have a boiling point which lies above the chosen reaction temperature or exactly corresponds to it.

The alkali metal salts of the aromatic o-hydroxycarboxylic acid derivatives to be used are preferably the sodium salts and potassium salts.

The starting materials are generally used in stoichiometric weight ratios, i.e. in equal molar amounts (1:1), but molar ratios of 1:2 to 2:1 are possible.

In view of the reaction temperature, a procedure employing reflux of the solvent or suspension medium is preferred.

The reaction according to the invention can be carried out in the presence of catalytic amounts of heterocyclic, aromatic compounds or quaternary ammonium or phosphonium salts, which accelerate the reaction of P—Cl groups with OH groups. For example, pyridines, preferably dimethylamino pyridines, quinolines or imidazoles are suitable as catalysts. When a catalyst is used, this can be supplied in amounts of 0.1 to 10 mol %, calculated on the aromatic o-hydroxycarboxylic acid used. In contrast, the addition of an acid binder, for example, a tertiary amine, in a roughly stoichiometric molar ratio to trap the hydrogen chloride in the reaction mixture is not advantageous, since in this case, as expected, compounds having a 6-ring structure of the type

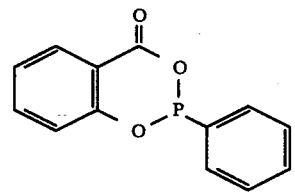

form.

The reaction temperature is generally selected in dependence on the reactivity of the starting materials. The duration of reaction is of secondary importance and is generally shorter when the reaction temperature is high. The duration of reaction can be between 2 and 100 hours.

The workup of the target products is carried out by standard methods of preparative organic chemistry. The target products are frequently crystalline and are isolated by filtration, if required after concentration or cooling of the reaction mixture. The crystals can be washed using the aprotic solvent and dried. Recrystallization instead of washing is frequently more advantageous.

With the use of alkali metal salts of the aromatic o-hydroxycarboxylic acids, the resulting alkali metal chloride must be removed either by filtration or by washing the reaction mixture or the separated off crude product using water.

EXAMPLE 1

Reaction of 2-hydroxy-1-naphthoic acid with phenyldichlorophosphine $PhPCl_2$

Phenyldichlorophosphine (6.6 g; 36.7 mmol) is added dropwise to a suspension of 2-hydroxy-1-naphthoic acid (6.9 g; 36.7 mmol) in isooctane (70 ml). On heating, HCl formation occurs and the solid liquefies. The two-phase reaction mixture is held at 90° C. for 4 h. On cooling, the lower, viscous, yellow layer crystallizes completely. The upper liquid is separated off and the residue is recrystallized from toluene. The product is obtained as a yellow, crystalline solid.

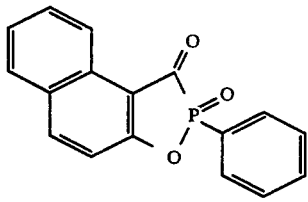

Formula:

Name: 3-oxo-2-phenylnaphtho[1,2-d]-1,2-oxaphospholane 2-oxide
Yield: 4.1 g (51.6% of theory)
Melting point: 142°–143° C.
NMR data:
$^{31}P$ (CDCl$_3$): 16.9 ppm;
$^1H$ (80 MHz, CDCl$_3$): 7.0–9.0 ppm (multiplet)
$^{13}C$ (50 MHz, CDCl$_3$):
197.9 ppm; doublet; J(C—P) 111.7 Hz; C=O;
168.4 ppm; doublet; J(C—P) 2.0 Hz; C—O;
142.8 ppm; singlet; C—H (naphtho-);
134.6 ppm; doublet; J(C—P) 2.96 Hz; C—H (naphtho-);
132.1 ppm; doublet; J(C—P) 12.15 Hz; C—H (phenyl-);
131.5 ppm; singlet; C—H (naphtho-);
130.0 ppm; doublet; J(C—P) 3.07 Hz; C (naphtho-);
129.3 ppm; doublet; J(C—P) 13.96 Hz; C—H (phenyl-);
128.9 ppm; singlet; C—H (phenyl-);
128.5 ppm; doublet; J(C—P) 13.05 Hz; C (naphtho-);
127.0 ppm; singlet; C—H (naphtho-);
123.7 ppm; singlet; C—H (naphtho-);
123.6 ppm; doublet; J(C—P) 120.9 Hz; C;
116.0 ppm; doublet; J(C—P) 73.4 Hz; C;
115.8 ppm; doublet; J(C—P) 5.1 ppm; C—H (naphtho)
MS (direct injection, 70 eV): m/e (I$_{rel}$, fragment):
294 (95, M+);
266 (100, M—CO7+);
217 (63, M—C$_6$H$_5$7+);
170 (47, M—C$_6$H$_5$-PO7+);
154 (18, M—C$_6$H$_5$PO$_2$7+);
142 (35, M—C$_6$H$_5$PO—CO7+);
126 (18, C$_{10}$H$_6$7+);
114 (46, C$_9$H$_6$7+);
UV (acetonitrile): maxima at 218, 251 and 339 nm.

EXAMPLE 2

Reaction of 2-hydroxy-1-naphthoic acid with phenyldichlorophosphine PhPCl$_2$

Phenyldichlorophosphine (86.6 g; 486 mmol) is added dropwise to a suspension of 2-hydroxy-1-naphthoic acid (91.2 g; 486 mmol) in xylene/toluene (300+500 ml). On heating, HCl formation occurs and the solution turns yellow. The naphthoic acid slowly dissolves with steady gas formation. The reaction mixture is stirred for 88 h at 117° C. A yellow solid crystallizes out on cooling. The crystals are separated off, washed using toluene and dried in vacuo.
Yield: 58.8 g (41.3% of theory)
NMR data: —P (CDCl$_3$):
17.1 ppm (isomer I);
12.6 ppm (isomer II).

EXAMPLE 3

Reaction of 2-hydroxy-1-naphthoic acid with phenyldichlorophosphine PhPCl$_2$

The reaction of Example 1 is repeated using 52.7 g (280 mmol) of 2-hydroxy-1-naphthoic acid and 50.1 g (280 mmol) of phenyldichlorophosphine in 250 ml of isooctane, 110 mg of 4-dimethylaminopyridine being added to the reaction mixture. After a reaction time of 4 h at 95° C. and recrystallization from toluene, a yellow, crystalline product is obtained.
Yield: 35 g (42.5% of theory)

EXAMPLE 4

Reaction of 2-hydroxy-1-naphthoic acid with phenyldichlorophosphine PhPCl$_2$

The reaction is carried out analogously to Example 1 using 18.1 g (96 mmol) of 2-hydroxy-1-naphthoic acid, 17.1 g (96 mmol) of phenyldichlorophosphine and 110 mg of 4-dimethylaminopyridine in methylene chloride (200 ml) for 24 h at 20° C., followed by 20 h at 40° C. According to P-NMR, the cyclic product is present in the reaction mixture upon completion of reaction at a purity of 91%.

EXAMPLE 5

Reaction of 2-hydroxy-1-naphthoic acid with methyldichlorophosphine MePCl$_2$ 250 mg of 4-dimethylaminopyridine are added to a suspension of 2-hydroxy-1-naphthoic acid (60 g; 319 mmol) in toluene (400 ml) and methyldichlorophosphine (37.7 g; 319 mmol) is then added dropwise. On heating, HCl formation occurs and the solid slowly dissolves. The reaction mixture is maintained at 40° C. for 24 h and at 100° C. for 7 h. After distilling off 150 ml of solvent, a light yellow solid crystallizes out on cooling.

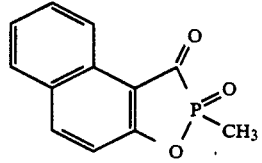

Formula:

Name: 2-methyl-3-oxonaphtho[1,2-d]-1,2-oxaphospholane 2-oxide
Yield: 23.1 g (31.2% of theory)
Melting point: 149°–152° C.
NMR data:
$^{31}P$ (CDCl$_3$): 29.6 ppm;
$^{13}C$ (24 MHz, CDCl$_3$/DMSO-d6):
197.6 ppm; doublet; J(C—P) 106.8 Hz; C=O;
168.4 ppm; singlet (not resolved); C—O
142.0 ppm; singlet; C—H (naphtho-);
130.5 ppm; singlet; C—H (naphtho-);
128.1 ppm; singlet;
126.1 ppm; singlet;
122.7 ppm; singlet;
115.8 ppm; doublet; J(C—P) 4.5 Hz;
115.0 ppm; doublet; J(C—P) 72.9 Hz;
10.2 ppm; doublet; J(C—P) 78.2 Hz; CH$_3$
other signals not assigned;
UV (acetonitrile): maxima at 217, 247 and 334 nm.

EXAMPLE 6

Reaction of 2-hydroxy-1-naphthoic acid with ethyldichlorophosphine EtPCl$_2$

As in Example 5, 2-hydroxy-1-naphthoic acid (54.9 g; 292 mmol) in toluene (400 ml), with addition of 250 mg of 4-dimethylaminopyridine, is reacted with ethyldichlorophosphine (38.2 g; 292 mmol). The reaction mixture is maintained at 40° C. for 24 h and at 100° C. for 5 h. After distilling off 200 ml of toluene, a light yellow solid crystallizes out on cooling.

Formula:

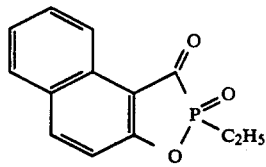

Name: 2-ethyl-3-oxonaphtho[1,2-d]-1,2-oxaphospholane 2-oxide

Yield: 18.2 g (25.3% of theory)
Melting point: 101°–102° C.
NMR data:
$^{31}$P (CDCl$_3$): 34.1 ppm;
$^{13}$C (24 MHz, CDCl$_3$/DMSO-d6):
197.8 ppm; doublet; J(C—P) 102.0 Hz; C=O;
167.2 ppm; singlet (not resolved); C—O
142.0 ppm; singlet; C—H (naphtho-);
115.5 ppm; doublet; J(C—P) 67.7 Hz;
115.0 ppm; doublet; J(C—P) 4.8 Hz;
18.8 ppm; doublet J(C—P) 96.6 Hz; CH$_2$ (isomer I);
18.1 ppm; doublet J(C—P) 75.9 Hz; CH$_2$ (isomer II);
4.8 ppm; not resolved; CH$_3$ (isomer I);
4.2 ppm; doublet; J(C—P) 4.5 Hz; CH$_3$ (isomer II);
other signals not assigned;
UV (acetonitrile): maxima at 217, 248 and 334 nm.

EXAMPLE 7

Reaction of 1-hydroxy-2-naphthoic acid with phenyldichlorophosphine PhPCl$_2$

Phenyldichlorophosphine (56.3 g; 315 mmol) is added dropwise to a suspension of 1-hydroxy-2-naphthoic acid (59.3 g; 315 mmol) in xylene (250 ml). On heating, HCl formation occurs and the solution turns yellow. The reaction mixture is stirred for 10 h at 110° C. and for 14 h at 25° C. 150 ml of solvent are then distilled off in a nitrogen stream (T=120° C.). A yellow solid crystallizes out on cooling.

Formula:

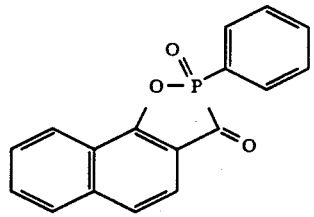

Name: 3-oxo-2-phenylnaphtho[2,1-d]-1,2-oxaphospholane 2-oxide

Yield: 33.7 g (36.4% of theory)
Melting point: 124°–126° C.
NMR data: $^{31}$P (CDCl$_3$/DMSO-d6):
17.9 ppm (isomer I);
13.5 ppm (isomer II);
UV (acetonitrile): maxima at 217, 248, 267, 296 and 318 nm.

We claim:

1. A cyclic acylphosphinic acid derivative of the formula

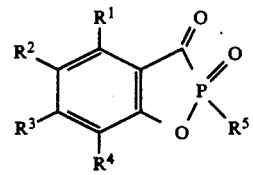

in which the substituents independently of each other can have the following meaning:

$R^1$, $R^2$, $R^3$, $R^4$=H, Cl, Br or C1- to C10-alkyl or -alkoxy, but on condition that either $R^1$ and $R^2$ together, or $R^3$ and $R^4$ together, with incorporation of the associated aromatic 6-ring, form a naphthalene structure;

$R^5$=C1- to C4-alkyl, C5- or C6-cycloalkyl, phenyl or alkylphenyl.

2. The cyclic acylphosphinic acid derivative of the formula as claimed in claim 1, wherein the naphthalene structure is substituted by one or more C1- to C10-alkyl or -alkoxy groups.

3. A process for the preparation of the cyclic acylphosphinic acid derivative as claimed in claim 1, which comprises reacting an aromatic o-hydroxycarboxylic acid of the formula

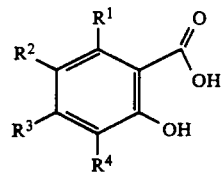

or an alkali metal salt thereof with an organyldichlorophosphine of the formula R$^5$PCl$_2$, where $R^1$, $R^2$, $R^3$, $R^4$ and $R^5$ have the meaning given, in an aprotic solvent or suspension medium at temperatures of 0° to 200° C. with liberation of gaseous hydrogen chloride or precipitation of alkali metal chloride and separating off and purifying the precipitated target product.

4. The process as claimed in claim 3, wherein the reaction is carried out in the presence of catalytic quantities of heterocyclic, aromatic compounds or quaternary ammonium salts or phosphonium salts.

* * * * *